United States Patent
Odaka et al.

(10) Patent No.: US 9,585,585 B2
(45) Date of Patent: Mar. 7, 2017

(54) ELECTRODE PAD

(71) Applicant: NIHON KOHDEN CORPORATION, Shinjuku-ku, Tokyo (JP)

(72) Inventors: Ryugo Odaka, Tokyo (JP); Michio Kanemoto, Tokyo (JP); Takeshi Akiyama, Tokyo (JP); Hideo Ozawa, Tokyo (JP); Tsutomo Wakabayashi, Tokyo (JP); Satoshi Hayashi, Tokyo (JP); Masakazu Yoshida, Tokyo (JP); Shigehiro Nishiwaki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 163 days.

(21) Appl. No.: 14/254,948

(22) Filed: Apr. 17, 2014

(65) Prior Publication Data
US 2014/0323841 A1    Oct. 30, 2014

(30) Foreign Application Priority Data

Apr. 25, 2013   (JP) .................................. 2013-092047
Mar. 28, 2014   (JP) .................................. 2014-068217

(51) Int. Cl.
*A61B 5/0408*    (2006.01)
*A61N 1/04*    (2006.01)

(52) U.S. Cl.
CPC .......... *A61B 5/04087* (2013.01); *A61N 1/046* (2013.01); *A61N 1/0496* (2013.01)

(58) Field of Classification Search
CPC .......................... A61B 5/0408; A61B 5/04087
USPC ................................. 600/391, 392, 395, 397
See application file for complete search history.

(56) References Cited

U.S. PATENT DOCUMENTS 4,674,512 A    6/1987   Rolf
6,845,272 B1   1/2005   Thomsen et al.

FOREIGN PATENT DOCUMENTS

EP   0 323 711 A1   7/1989

OTHER PUBLICATIONS

Search Report dated Jul. 30, 2014 issued by the European Patent Office in counterpart European Patent Application No. 14165111.7.

*Primary Examiner* — Lee S Cohen
(74) *Attorney, Agent, or Firm* — Sughrue Mion, PLLC

(57) ABSTRACT

An electrode pad includes: a conductor layer; and an adhesive gel layer which is stacked on one surface of the conductor layer, the adhesive gel layer which contains 0.1 wt % or more of SnCl2.2H2O, and which has a pH of 3 to 6. The conductor layer may a conductive metal layer. The conductor layer may include a tin foil.

6 Claims, 5 Drawing Sheets

ELECTRODE PAD

CROSS-REFERENCE TO RELATED APPLICATION(S)

This application is based upon and claims the benefit of priority from prior Japanese patent applications No. 2013-092047, filed on Apr. 25, 2013 and No. 2014-068217, filed on Mar. 28, 2014 the entire contents of which are incorporated herein by reference.

BACKGROUND

The presently disclosed subject matter relates to an electrode pad having an adhesive gel layer, and particularly to an electrode pad in which noises caused by chest compression or the like can be reduced.

In order to perform rescue from a cardiac arrest state due to ventricular fibrillation (VF), recently, not only public facilities but also offices, convenience stores, and the like are equipped with an AED (Automatic External Defibrillator). An AED is used for, when ventricular fibrillation or the like occurs, applying a strong defibrillation shock (electric shock) to the heart to eliminate a cramp in the heart muscle.

On the other hand, cardiopulmonary resuscitation (CPR) is known as a method of maintaining a chance of rescuing a person who seems to stop breathing and have no cardiac activity. According to 2010 AHA (American Heart Association) Guidelines and JRC (Japan Resuscitation Council) Guidelines 2010 which show a procedure of performing CPR, it is recommended to perform chest compression in advance of defibrillation with an AED.

In a rescue procedure in which the lifesaving rate becomes lower as time elapses, it is preferable that the period required for automatic electrocardiogram analysis performed by an AED is as short as possible. When chest compression is performed in advance of defibrillation with an AED, however, noises caused by chest compression affect the automatic electrocardiogram analysis, so that the analysis is hardly performed. Therefore, chest compression is interrupted until the automatic electrocardiogram analysis performed by an AED is completed.

An electrode pad is known in which, in order to check as soon as possible the effect of defibrillation applied to a patient in ventricular fibrillation, a strong acid gel is used in the electrode pad as means for reducing a high DC offset voltage generated on the electrode pad (see U.S. Pat. No. 6,845,272).

As an electrode pad which has a low DC offset voltage and a low impedance, and in which the S/N ratio is high, an electrode pad having a soft conductive electrode configured by Sn, and a gel containing tin salts is known (see U.S. Pat. No. 4,674,512).

In the electrode pad which is disclosed in U.S. Pat. No. 6,845,272, and in which a strong acid gel is used as a gel, in order to assure a long storage period, however, a metal layer in an electrode must be thick in consideration of corrosion due to oxidation of the electrode. When the metal layer is thick, the flexibility of the electrode pad is lowered, and the contacting property with respect to the skin is impaired. In a worse condition, there may arise a problem in that the skin is burned during defibrillation. In the case of an electrode pad using a strong acid gel, the skin irritation is so high that inflammation may occur. In order to prevent this from occurring, a double-layer gel structure in which a weak acid gel is formed on the side of the skin is employed.

Moreover, the electrode pad which is disclosed in U.S. Pat. No. 4,674,512 cannot provide an electrocardiogram waveform which enables automatic electrocardiogram analysis to be performed during cardiopulmonary resuscitation by chest compression.

SUMMARY

The presently disclosed subject matter may provide an electrode pad in which the influence of noises caused by CPR or the like can be made very small.

The electrode pad may comprise: a conductor layer; and an adhesive gel layer which is stacked on one surface of the conductor layer, the adhesive gel layer containing 0.1 wt % or more of $SnCl_2.2H_2O$, and having a pH of 3 to 6.

The conductor layer may include a conductive metal layer.

The conductor layer may include a tin foil.

The conductor layer may have an area of 50 $cm^2$ or more, and the electrode pad may be for an adult.

The conductor layer may have an area of 15 $cm^2$ or more, and the electrode pad may be for a child.

DETAILED DESCRIPTION OF EXEMPLARY EMBODIMENTS

Figure 1:
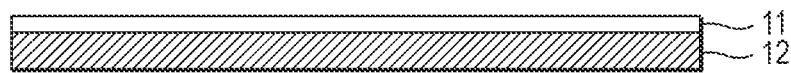
FIG. 1 is a sectional view showing an embodiment of the electrode pad of the presently disclosed subject matter.

Hereinafter, an embodiment of the electrode pad of the presently disclosed subject matter will be described with reference to the accompanying drawings. A sectional view of the embodiment of the electrode pad of the presently disclosed subject matter may be as shown in FIG. 1. For example, the electrode pad includes a conductor layer 11 configured by a conductive metal layer, and an adhesive gel layer 12 which is stacked on one surface of the conductor layer 11.

The conductor layer 11 may be configured by a tin foil. For example, the adhesive gel layer 12 contains 0.1 wt % or more of $SnCl_2.2H_2O$ with respect to a conductive adhesive composition (for example, a composition similar to that of JP-A-2005-213455 of the patent application assigned to the same assignee of the present application) which will be used as a gel layer of a biological electrode. Moreover, the pH of the adhesive gel layer 12 is set to 3 to 6.

It is a matter of course that the thicknesses of the above-described conductor layer 11 and adhesive gel layer 12 can be adequately changed in accordance with the use of the electrode pad. As the plan shape of the electrode pad, one of a circle, an ellipse, a rectangle, a polygon, and the like may be employed. Corner portion of the electrode pad may be cut into an arcuate shape. Although the conductor layer 11 is configured by a tin foil, the conductor layer may be configured by another material such as silver.

In the international standard IEC 60601-2-4, it is specified that the area of a conductive portion for an adult is 50 cm$^2$ or more, and that for a child is 15 cm$^2$ or more. Preferably, the conductor layer 11 has a mode according to the standard.

In the conductor layer 11, the surface which is not in contact with the adhesive gel layer 12 may be adequately insulated. An insulating sheet or the like is disposed on the surface. In the adhesive gel layer 12, a peel-off sheet may be pasted to the surface which is not in contact with the conductor layer 11. In the electrode pad to which a peel-off sheet is pasted, when the electrode pad is to be used, the peel-off sheet is first peeled off, and then the electrode pad is used. A lead wire through which a signal is output, or to which is used for applying defibrillation to a living body is applied is connected to the conductor layer 11.

Comparative experiments using a swine were performed on electrode pads (Samples A1 to A4) which do not contain SnCl2.2H2O, and electrode pads (Samples B1 to B4) (containing SnCl2.2H2O) which were prepared so as to have the configuration of the presently disclosed subject matter. In Samples A1 to A4 and Samples B1 to B4, the pH and the concentration (wt %) of SnCl2.2H2O are as shown in Table 1 below.

TABLE 1

| Sample No. | pH | Concentration of SnCl2•2H2O |
|---|---|---|
| A1 to A4 | 5.26 | 0% |
| B1 to B4 | 4.69 | 0.2% |

While using Samples A1 to A4 and Samples B1 to B4, chest compression was applied on a swine by using chest compressing means: (1) a person manually applied chest compression as CPR to a swine (manual); and (2) chest compression was applied as CPR by a machine to a swine (mechanical), and electrocardiograms were obtained.

The states of the electrocardiograms of the employed swine were the ventricular fibrillation state and the asystole state. At this time, relationships of the states of the electrocardiograms, the chest compressing means, the kinds of samples, and the samples are as shown in Table 2 below.

TABLE 2

| State of electrocardiogram | Chest compressing means | Kind of sample | Sample No. |
|---|---|---|---|
| Ventricular fibrillation | Manual | Related-art | A1 |
| Ventricular fibrillation | Manual | Subject matter | E1 |
| Ventricular fibrillation | Mechanical | Related-art | A2 |
| Ventricular fibrillation | Mechanical | Subject matter | B2 |
| Asystole | Manual | Related-art | A3 |
| Asystole | Manual | Subject matter | B3 |
| Asystole | Mechanical | Related-art | A4 |
| Asystole | Mechanical | Subject matter | B4 |

Figure 2:
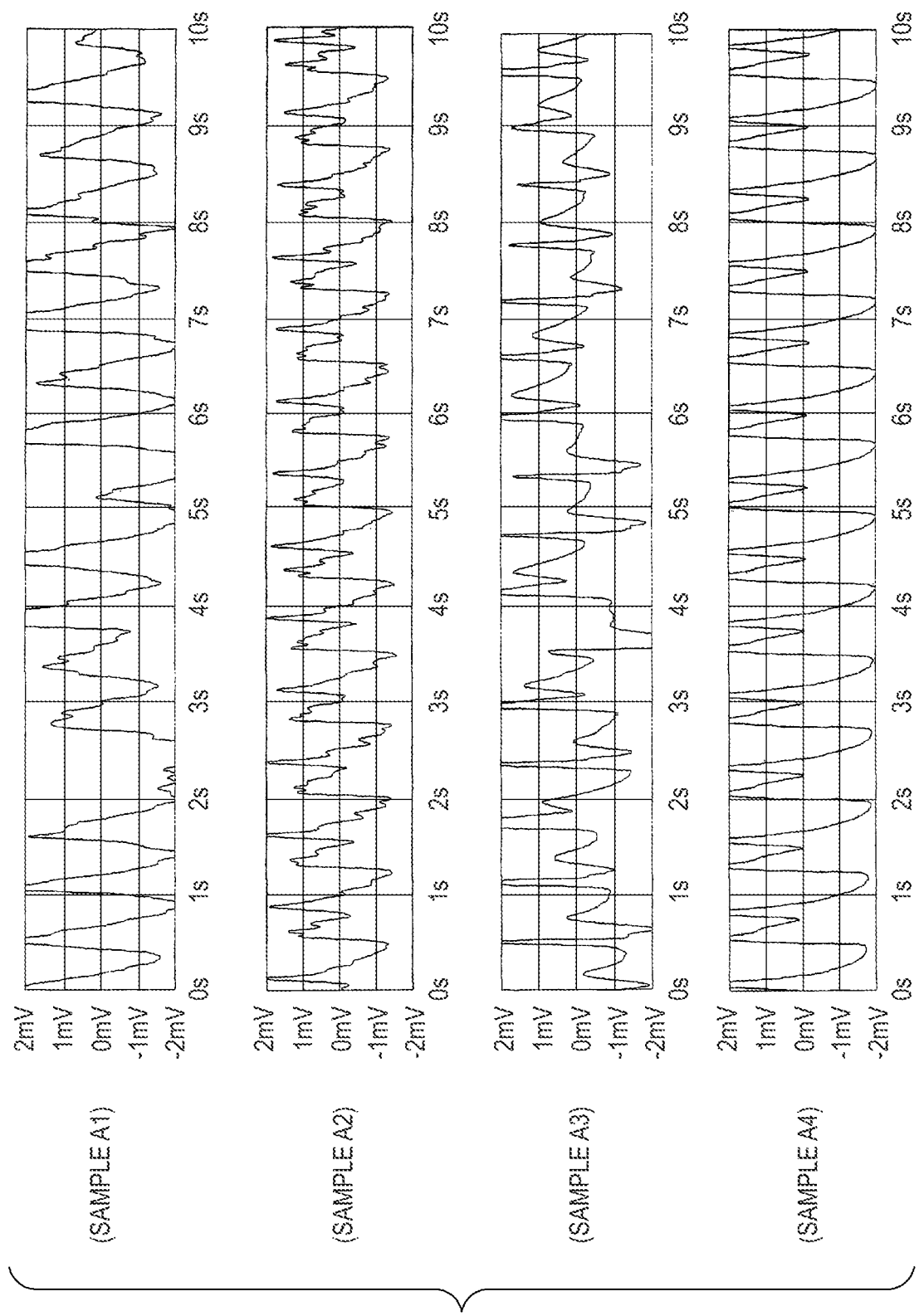
FIG. 2 is a view showing results of comparative experiments of noise generation during chest compression in an electrode pad of a related-art product.
Figure 3:
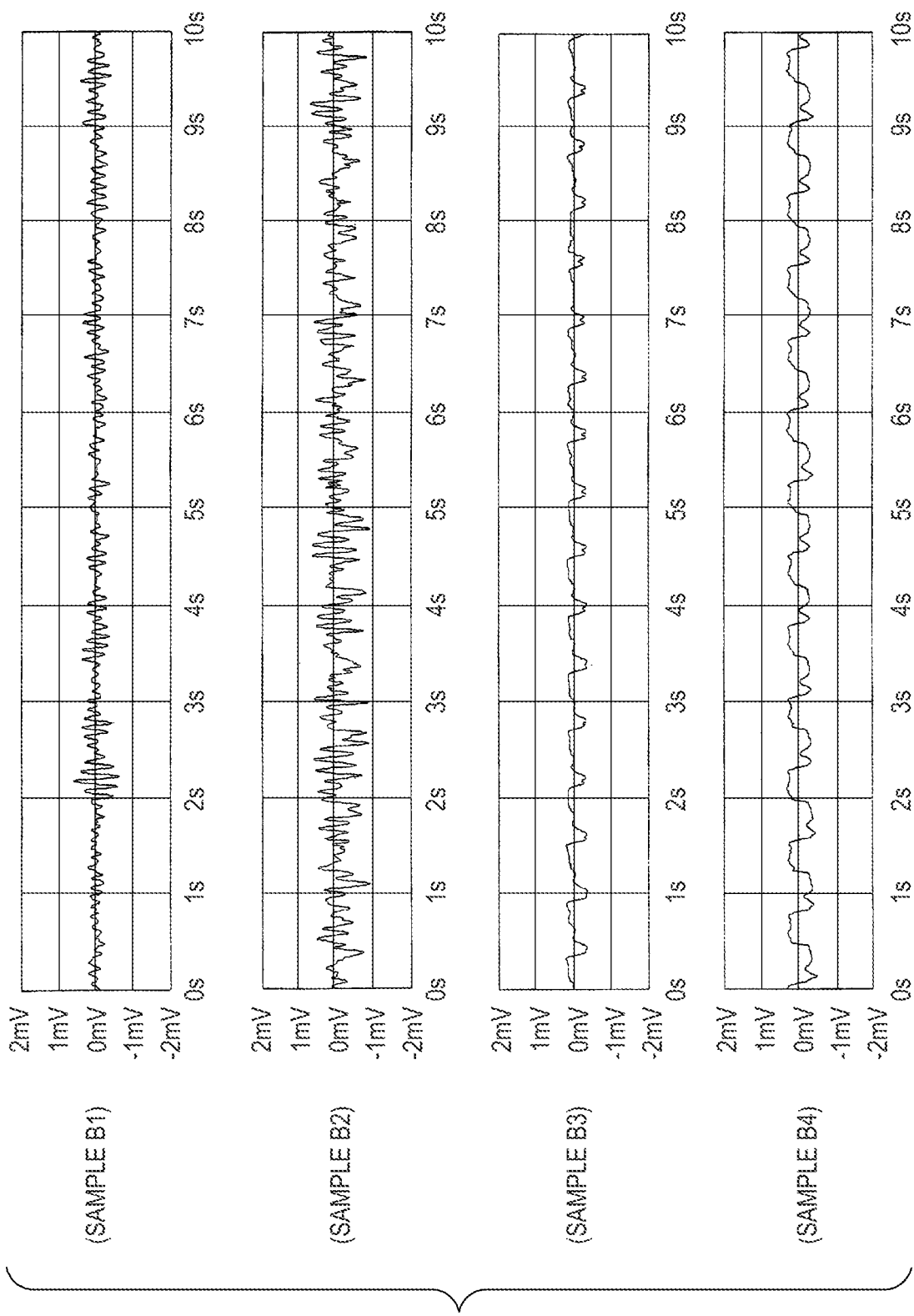
FIG. 3 is a view showing results of comparative experiments of noise generation during chest compression in the embodiment of the electrode pad of the presently disclosed subject matter.

FIGS. 2 and 3 show electrocardiograms which were obtained during above described chest compression. As seen from comparison of FIGS. 2 and 3, in the case where electrode pads having the configuration of the presently disclosed subject matter are used, noises caused by chest compression do not appear in the electrocardiograms, and it is expected that an electrocardiogram measurement can be adequately performed.

Figure 4:
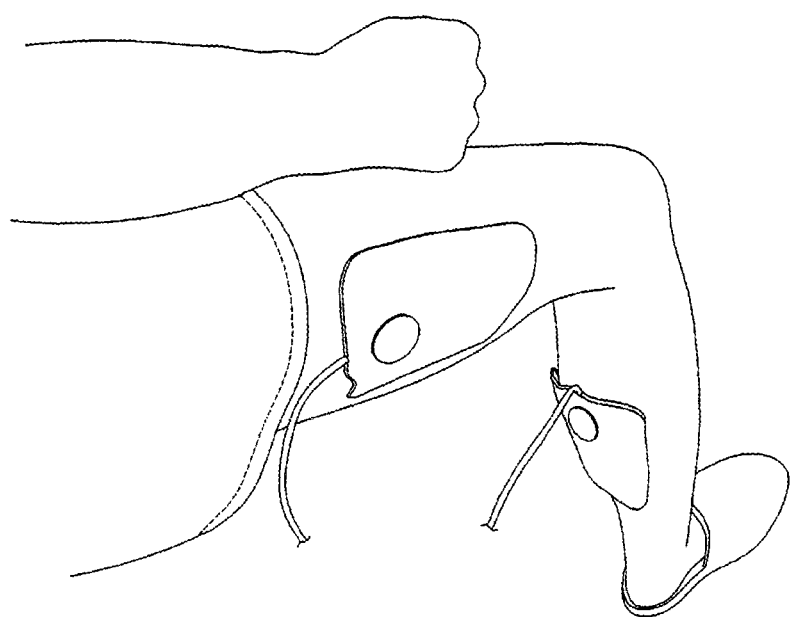
FIG. 4 is a view showing experiments of pseudo-chest compression in the embodiment of the electrode pad of the presently disclosed subject matter and a related-art product.

With respect to electrode pads which were produced as indicated in Table 3, and related-art electrode pads which were commercially obtained, noises caused by pseudo-chest compression were measured in the following manner. As shown in FIG. 4, electrode pads were pasted to the outer side of a thigh of one leg of a volunteer, and the calf of the leg, respectively. As pseudo-chest compression, a front portion of the thigh was punched. Noises caused by pseudo-chest compression at this time were measured.

TABLE 3

| Contents of evaluation samples | Sample No. |
|---|---|
| Produced electrode pads including those of presently disclosed subject matter | S1, S3, S9 to S13 |
| Related-art electrode pads which were commercially obtained | T2, T4 to T8 |

Figure 5:
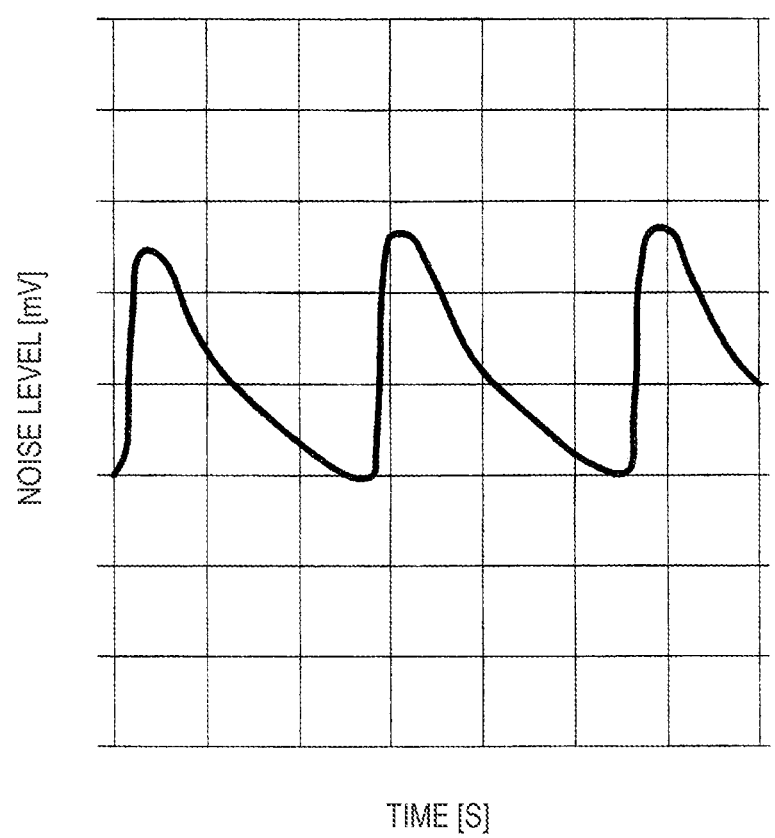
FIG. 5 is a view showing noises during pseudo-chest compression in the electrode pad of the presently disclosed subject matter.

This is because of the following reasons. Even when noises caused by chest compression or the like occur in electrode pads, in-phase components are canceled out because a bipolar lead (differential input) is derived between the electrode pads. Also in the case where electrocardiograms overlap with each other, it is difficult to correctly quantify generated noises. In order to correctly quantify noises generated in electrode pads, the front portion of the thigh was punched as pseudo-chest compression. As portions where electrocardiograms do not overlap with each other, one of the electrode pads was pasted to the outer side of the thigh which is susceptible to be affected by noises, and the other electrode pad was pasted to the calf which is not substantially affected by noises. Noise levels in the electrode pads of the presently disclosed subject matter were compared with those of the related-art electrode pads. FIG. 5 shows an example of noises caused by pseudo-chest compression at this time. Then, the results were determined by the determination criteria of Table 4. The symbol "a" indicates a level at which noises are not substantially generated, "c" indicates a level of about 1.0 mV to which corresponds to 2 scale steps in the graphs of FIGS. 2, 3, and 5, and "d" indicates a noise level of about 1.5 mV or higher which corresponds to 3 scale steps.

TABLE 4

| Symbol | Level of noises caused by pseudo-chest compression |
|---|---|
| a | about 0.0 mV (0 scale step) |
| b | about 0.5 mV (1 scale step) |
| c | about 1.0 mV (2 scale steps) |
| d | about 1.5 mV (3 scale steps) or higher |

Table 5 shows results of the above-described determinations. As apparent from the column of noises caused by pseudo-chest compression in Table 5, when electrode pads having the configuration of the presently disclosed subject matter are used in an actual emergency rescue site, the influence of noises caused by chest compression does not appear in an electrocardiogram, and it is expected that an electrocardiogram measurement can be adequately performed.

TABLE 5

| Sample No. | Noises caused by pseudo-chest compression | pH | Concentration of SnCl2·2H2O |
|---|---|---|---|
| S1 | d | 7.18 | 0.0% |
| T2 | c | 6.75 | 0.0% |
| S3 | a | 6.00 | 0.5% |
| T4 | d | 5.55 | 0.0% |
| T5 | d | 5.54 | 0.0% |
| T6 | d | 5.54 | 0.0% |
| T7 | d | 5.52 | 0.0% |
| T8 | d | 5.26 | 0.0% |
| S9 | a | 4.69 | 0.2% |
| S10 | a | 3.71 | 1.0% |
| S11 | a | 3.54 | 0.5% |
| S12 | a | 3.45 | 0.1% |
| S13 | a | 3.06 | 1.3% |

As shown in FIG. 1, in the electrode pad, the adhesive gel layer is stacked on one surface of the conductor layer. However, the conductor layer includes a portion which is not covered by the gel layer. With respect to electrode pads having the configuration of the presently disclosed subject matter, electrode pads immediately after production, and those which had been stored for 24 months (stored at room temperature) were subjected to measurements of thicknesses of the conductor layer which is not cover by the adhesive gel layer and the conductor layer which is covered by the adhesive gel layer. Table 6 shows comparisons of the measurement results.

TABLE 6

| Sample A | Conductor layer which is not covered by adhesive gel layer 73.630 to 79.110 μm<br>Conductor layer which is covered by adhesive gel layer 76.715 to 77.740 μm |
|---|---|
| Sample B | Conductor layer which is not covered by adhesive gel layer 67.809 to 71.918 μm<br>Conductor layer which is covered by adhesive gel layer 69.521 to 69.863 μm |

Electrodes pads of Sample A are those immediately after production, and electrode pads of Sample B are those which had been stored for 24 months. In both Sample A and Sample B, measurement was conducted at a plurality of places on each electrode pad. In the results, therefore, the measurement values have a certain width. According to Table 6, in Sample A, the thickness of the conductor layer which is not covered by the adhesive gel layer is substantially identical with that of the conductor layer which is covered by the adhesive gel layer, and, also in Sample B, the thickness of the conductor layer which is not covered by the adhesive gel layer is substantially identical with that of the conductor layer which is covered by the adhesive gel layer. As a result, it was concluded that the conductor layer is not dissolved (eroded) by the adhesive gel layer, and the electrode pad can be stored for a long term.

With respect to an electrode pad not having the configuration of the presently disclosed subject matter, the initial thickness which was obtained immediately before storage, and the thickness which was obtained after storage of about 2 years (storage at room temperature) were measured. Table 7 shows comparisons of the measurement results.

TABLE 7

| Initial thickness | 50 μm (0.05 mm) |
|---|---|
| Thickness after storage of about 2 years | 40 μm (0.04 mm) |

According to the table, as a result of the storage of about 2 years, the thickness of the conductor layer was reduced from 50 μm to 40 μm, or by 20%. The thickness change of the conductor layer is remarkably larger than that of the samples shown in Table 6. As a result, the superiority of an electrode pad having the configuration of the presently disclosed subject matter was proved.

The electrode pad of the embodiment has been demonstrated to be particularly useful as a defibrillation electrode pad and an AED electrode pad. The electrode pad of the presently disclosed subject matter is useful as a defibrillation electrode pad and an AED electrode pad, and, because of the above-described features such as a low noise level, expected to be employed as an electrode pad which is preferably used as a transcutaneous pacing electrode pad, an electrocardiogram electrode pad, a return electrode, and the like.

According to an aspect of the presently disclosed subject matter, in the configuration including the conductor layer, and the adhesive gel layer which is stacked on one surface of the conductor layer, when the adhesive gel layer contains 0.1 wt % or more of SnCl2.2H2O and the pH of the adhesive gel layer is in the range of 3 to 6, noises from the skin can be drastically reduced. In the case where an electrocardiogram measurement is performed during chest compression conducted as CPR, particularly, the electrocardiogram measurement can be performed without being affected by noises.

Since a strong acid gel is not used, it is not necessary to increase the thickness of the metal layer of the electrode in consideration of corrosion due to oxidation of the electrode, and therefore an electrode pad which is thin, and which has an excellent attaching property can be provided. Moreover, to corrosion due to oxidation does not occur, and the adhesive gel layer contains 0.1 wt % or more of SnCl2.2H2O. Therefore, the electrode pad has an advantage that the electrode pad can be stored for a long term while maintaining the low-noise state.

What is claimed is:

1. An electrode pad comprising:
a conductor layer; and
an adhesive gel layer which is stacked on one surface of the conductor layer, the adhesive gel layer containing 0.1 wt % or more of SnCl2.2H2O, and the adhesive gel layer having a pH of 3 to 6,
wherein the electrode pad is configured to be connected to a defibrillator, and the electrode pad is configured to apply an electric shock and to obtain an electrocardiogram.

2. The electrode pad according to claim 1, wherein the conductor layer includes a conductive metal layer.

3. The electrode pad according to claim 1, wherein the conductor layer includes a tin foil.

4. The electrode pad according to claim 1, wherein the conductor layer has an area of 50 cm$^2$ or more, and the electrode pad is for an adult.

5. The electrode pad according to claim 1, wherein the conductor layer has an area of 15 cm$^2$ or more, and the electrode pad is for a child.

6. An electrode pad comprising:
a conductor layer; and
an adhesive gel layer which is stacked on one surface of the conductor layer, the adhesive gel layer containing 0.1 wt % or more of SnCl2.2H2O, and the adhesive gel layer having a pH of 3 to 6, wherein the electrode pad is configured to obtain an electrocardiogram without being affected by a noise caused by chest compression.

\* \* \* \* \*